(12) United States Patent
Yamakawa (10) Patent No.: US 10,288,120 B2
(45) Date of Patent: May 14, 2019

(54) ROLLING BEARING, ROTATING MACHINE ELEMENT, AND SOLID-FILM FORMATION METHOD

(71) Applicant: JTEKT CORPORATION, Osaka-shi, Osaka (JP)

(72) Inventor: Kazuyoshi Yamakawa, Nishinomiya (JP)

(73) Assignee: JTEKT CORPORATION, Osaka (JP)

( * ) Notice: Subject to any disclaimer, the term of this patent is extended or adjusted under 35 U.S.C. 154(b) by 157 days.

(21) Appl. No.: 15/614,716

(22) Filed: Jun. 6, 2017

(65) Prior Publication Data

US 2017/0356499 A1    Dec. 14, 2017

(30) Foreign Application Priority Data

Jun. 10, 2016   (JP) .................................. 2016-116097

(51) Int. Cl.
| | |
|---|---|
| *C07C 69/54* | (2006.01) |
| *C08G 65/00* | (2006.01) |
| *F16C 33/38* | (2006.01) |
| *F16C 33/44* | (2006.01) |
| *F16C 33/64* | (2006.01) |
| *F16C 33/66* | (2006.01) |

(Continued)

(52) U.S. Cl.
CPC .......... *F16C 33/6696* (2013.01); *C07C 69/54* (2013.01); *C08G 65/007* (2013.01); *C10M 107/38* (2013.01); *C10M 141/12* (2013.01); *C10M 161/00* (2013.01); *C10M 177/00* (2013.01); *F16C 33/445* (2013.01); *F16C 33/64* (2013.01); *C10M 2207/121* (2013.01); *C10M 2209/084* (2013.01); *C10M 2211/022* (2013.01); *C10M 2227/04* (2013.01); *C10M 2229/00* (2013.01); *C10N 2230/06* (2013.01); *C10N 2240/02* (2013.01); *F16C 33/38* (2013.01); *F16C 33/6648* (2013.01)

(58) Field of Classification Search
CPC .... F16C 33/6696; F16C 33/38; F16C 33/445; F16C 33/64; F16C 33/6648; C10M 107/38; C10M 131/12; C10M 161/00; C10M 177/00; C10M 2207/121; C10M 2209/084; C10M 2211/022; C10M 2227/04; C10M 2229/00; C10N 2230/06; C10N 2240/02
See application file for complete search history.

(56) References Cited

U.S. PATENT DOCUMENTS

| | | | |
|---|---|---|---|
| 5,939,363 A | 8/1999 | Toyota et al. | |
| 2002/0097936 A1* | 7/2002 | Yokouchi | F16C 33/62 384/492 |

FOREIGN PATENT DOCUMENTS

JP    H09-137830 A    5/1997

* cited by examiner

*Primary Examiner* — James C Goloboy
(74) *Attorney, Agent, or Firm* — Oliff PLC (57) ABSTRACT

A method is provided that forms a solid film on a bearing component of a rolling bearing. A solution containing a fluorine compound and a lubricant having no functional group is allowed to adhere to the bearing component as a first liquid film (adhesion step). The adhering first liquid film is hardened to form the solid film on the bearing component. The rolling bearing including the bearing component with the solid film formed thereon is rotated. The rolling bearing is washed in a washer fluid containing the same lubricant as that used in the adhesion step, and the washer fluid is allowed to adhere to the bearing component as a second liquid film. Then, the adhering second liquid film is dried.

9 Claims, 10 Drawing Sheets

(51) Int. Cl.
*C10M 107/38* (2006.01)
*C10M 141/12* (2006.01)
*C10M 161/00* (2006.01)
*C10M 177/00* (2006.01)

DUST PARTICLE GENERATION TEST CONDITIONS

| ROTATION SPEED | 200rpm |
|---|---|
| AXIAL LOAD | 50N (SPRING PRELOAD) |
| TEMPERATURE | ROOM TEMPERATURE |
| SUCTION SPEED | 0.1cf/10min |
| EVALUATION SUCTION AMOUNT | 1cf (FOR TEN MEASUREMENTS) |
| MEASURED PARTICLE SIZE | 0.1 $\mu$m OR MORE |
| ATMOSPHERE | AIR (IN CLEAN BENCH, CLASS 10) |
| EVALUATION ITEM | NUMBER OF DUST PARTICLES GENERATED WITH PARTICLE SIZE OF 0.1 $\mu$m OR MORE |

FIG. 10

ROLLING BEARING, ROTATING MACHINE ELEMENT, AND SOLID-FILM FORMATION METHOD

INCORPORATION BY REFERENCE

The disclosure of Japanese Patent Application No. 2016-116097 filed on Jun. 10, 2016 including the specification, drawings and abstract, is incorporated herein by reference in its entirety.

BACKGROUND OF THE INVENTION

1. Field of the Invention

The invention relates to a rolling bearing, a rotating machine element, and a solid-film formation method.

2. Description of the Related Art

When a rolling bearing is used in a vacuum environment or a corrosive environment in which the use of grease or oil is precluded, bearing components such as an inner ring and an outer ring are provided with a film-like coating formed of a solid lubricant. The coating is conventionally formed of, for example, soft metal such as gold, silver, or lead, or a layer structure material such as graphite or molybdenum disulfide.

When the rolling bearing is provided with the coating formed of the solid lubricant, a slight amount of solid lubricant peels off during rotation of the bearing to contribute to lubrication. The use of the coating reduces the number of dust particles from the rolling bearing compared to the use of grease or oil. Nevertheless, in an environment that needs high cleanliness, the application of the coating poses a problem. Thus, a rolling bearing has been proposed in which bearing components are provided with a solid film of a fluorine-containing polyurethane polymer compound (for example, Japanese Patent Application Publication No. H9-137830 (JP H9-137830 A)).

The technique described in JP H9-137830 A provides a bearing that is suitable in a vacuum environment, a corrosive environment, and a clean environment in which the use of grease or oil is precluded.

SUMMARY OF THE INVENTION

An object of the invention is to provide a rolling bearing and a rotating machine element that enable a reduction in the number of dust particles generated and improvement of lubricity and a solid-film formation method for manufacturing the rolling bearing or the rotating machine element.

The invention provides a solid-film formation method for forming a solid film on at least one of bearing components of a rolling bearing including an inner ring, an outer ring, and a plurality of rolling elements interposed between the inner ring and the outer ring. The solid-film formation method includes allowing a solution containing a fluorine compound and a lubricant having no functional group to adhere to the at least one of the bearing components as a first liquid film, forming a solid film on the at least one of the bearing components by hardening the adhering first liquid film, rotating the rolling bearing including the bearing component provided with the solid film, washing the rolling bearing in a washer fluid containing the same lubricant as the lubricant used in allowing the solution to adhere to the bearing component and allowing the washer fluid to adhere to the bearing component as a second liquid film, and drying the adhering second liquid film.

BRIEF DESCRIPTION OF THE DRAWINGS

The foregoing and further features and advantages of the invention will become apparent from the following description of example embodiments with reference to the accompanying drawings, wherein like numerals are used to represent like elements and wherein.

DETAILED DESCRIPTION OF EMBODIMENTS

Figure 1:
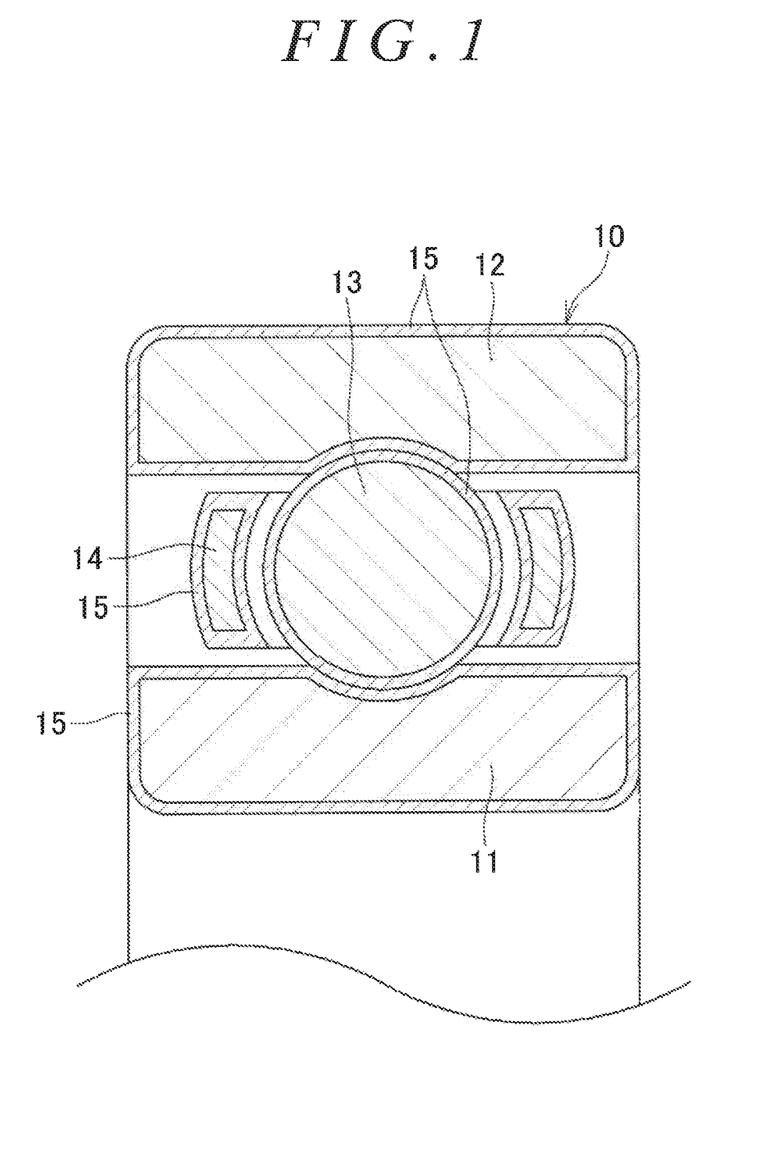
FIG. 1 is a sectional view depicting an embodiment of a rolling bearing in the invention.

FIG. 1 is a sectional view depicting an embodiment of a rolling bearing in the invention. A rolling bearing 10 includes an inner ring 11, an outer ring 12, a plurality of rolling elements 13, and a cage 14. In the embodiment depicted in FIG. 1, the rolling elements are balls 13. In other words, the rolling bearing 10 is a ball bearing. A cage 14 is an annular member that holds the balls 13 at intervals in a circumferential direction. The inner ring 11, the outer ring 12, the balls 13, and the cage 14 are each referred to as a bearing component. In the present embodiment, a solid film 15 is formed on a surface of each bearing component.

The inner ring 11, the outer ring 12, the balls 13, and the cage 14 in the present embodiment are formed of a material with corrosion resistance. The material with corrosion resistance may be, for example, martensitic stainless steel, austenitic stainless steel, or ceramics material. Instead of the corrosion-resistant material, carbon steel such as bearing steel may be used to form inner ring 11, the outer ring 12, the balls 13, and the cage 14. The cage 14 may be formed of brass or a synthetic resin material.

The solid film 15 is formed all over the surface of each of the inner ring 11, the outer ring 12, the balls 13, and the cage 14. The solid film 15 is formed of a fluorine compound containing 3-(trimethoxysilyl) propyl methacrylate, hexafluoropropene, and methyl methacrylate as monomer components.

Figure 2:
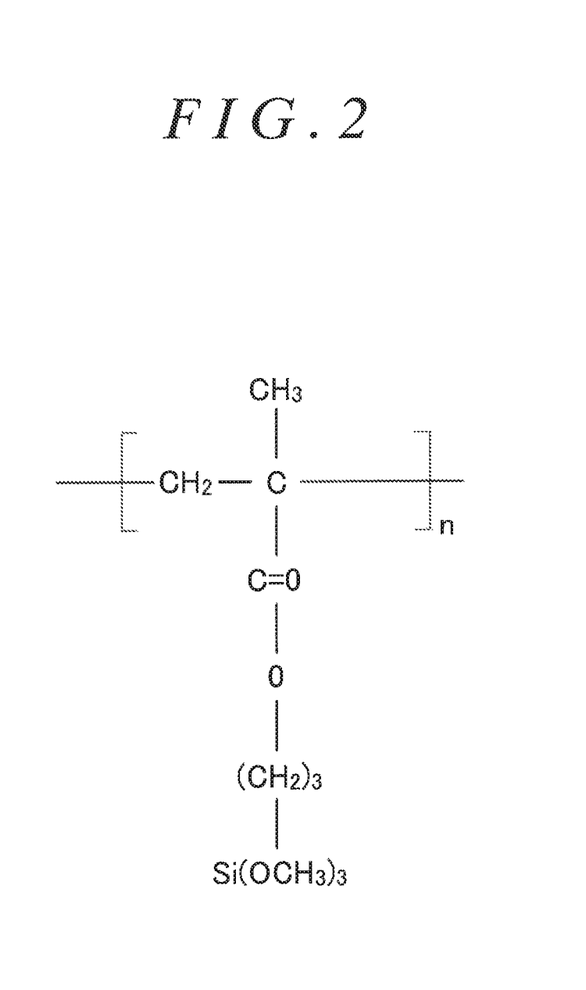
FIG. 2 is a diagram depicting a general formula (chemical formula) of 3-(trimethoxysilyl) propyl methacrylate.
Figure 3:
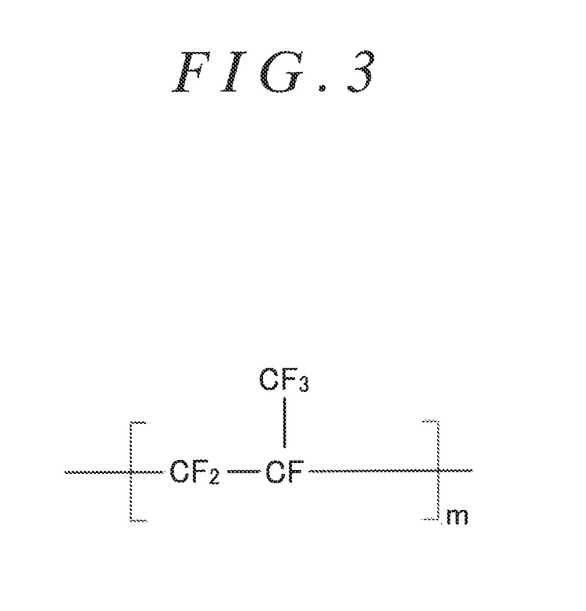
FIG. 3 is a diagram depicting a general formula (chemical formula) of hexafluoropropene.
Figure 4:
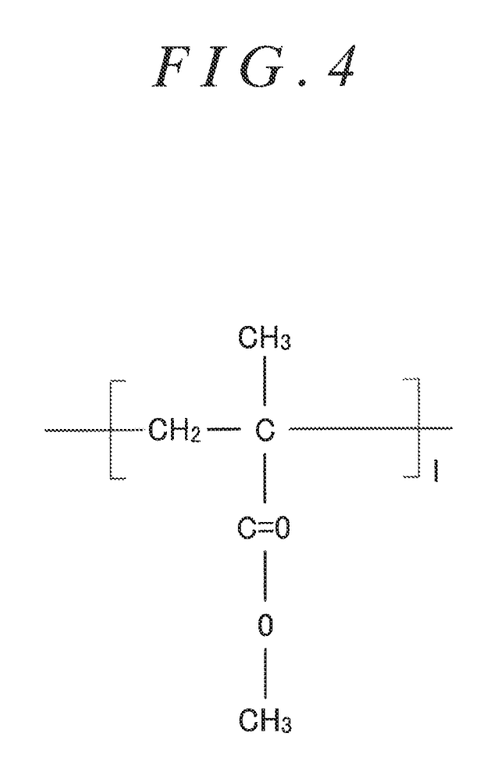
FIG. 4 is a diagram depicting a general formula (chemical formula) of methyl methacrylate.

FIG. 2 depicts a general formula (chemical formula) illustrating the structure of 3-(trimethoxysilyl) propyl methacrylate. FIG. 3 depicts a general formula (chemical formula) illustrating the structure of hexafluoropropene. FIG. 4 depicts a general formula (chemical formula) illustrating the structure of methyl methacrylate.

The solid film 15 contains a lubricant dispersively added thereto and having no functional group such that the lubricant can flow out from the solid film 15. The lubricant is a fluorine polymer, and in the present embodiment, contains perfluoropolyether (also hereinafter referred to as PFPE oil). The solid film 15 contains the lubricant (fluorine polymer) that is dispersively added to the solid film and that is a fluorine-based lubricant (fluorine-based lubricating oil) having no functional group. A surface of the solid film 15 is covered with the lubricant of the fluorine polymer. The solid film 15 is, for example, one to several maicrometers in thickness.

A formation method for the solid film 15 will be described. In the assembled state, the inner ring 11, the outer ring 12, the balls 13, and the cage 14 have been degreased. In this regard, in the present embodiment, the assembled rolling bearing 10 is degreased.

A solution described below is prepared, and the assembled rolling bearing 10 is immersed in the solution. The inner ring 11 and the outer ring 12 are rotated several times relative to each other. Consequently, a liquid film (in other words, a film of the solution) can be allowed to adhere to the entire surface of each of the inner ring 11, the outer ring 12, the balls 13, and the cage 14 (adhesion process).

The solution has a fluorine compound containing 3-(trimethoxysilyl) propyl methacrylate, hexafluoropropene, and methyl methacrylate as monomer components, and further contains the lubricant (perfluoropolyether) that is a fluorine polymer. The fluorine compound has functional groups, whereas the lubricant has no functional group. The solution will further be described. A first solute refers to the fluorine compound containing 3-(trimethoxysilyl) propyl methacrylate, hexafluoropropene, and methyl methacrylate as monomer components. A second solute refers to perfluoropolyether (PFPE oil) having no functional group. The solution is prepared by diluting the first solution with a solvent and adding the second solute to a solution resulting from the dilution. The solvent is a fluorine solvent, specifically, a mixture of ethyl nonafluoroisobutyl ether and ethyl nonafluorobutylether.

In the solution, preferably, the first solute is 0.5 to 5 wt % in concentration, whereas the second solute is 0.1 to 2 wt % in concentration. When the first solute is less than 0.5 wt %, the resultant solid film 15 is a thin soft film, possibly leading to a reduced friction resistance effect. When the first solute is more than 5 wt % in concentration, the bearing components are firmly stuck together via the solid film 15. Then, unsticking the bearing components may be difficult. Thus, the first solute is preferably 1 to 3 wt % in concentration. When the second solute is less than 0.1 wt % in concentration, the lubricant may produce a reduced lubrication effect. When the second solute is more than 2 wt % in concentration, the resultant solid film 15 may have low adhesion. Thus, the second solute is more preferably 0.3 to 1 wt % in concentration.

Mixture of the first solute (the above-described fluorine compound) and the second solute (perfluoropolyether) is preferably such that the amount of the first solute is larger than the amount of the second solute in order to provide the solid film 15 with the appropriate adhesiveness. That is, the mixture ratio between the first solute and the second solute is preferably such that the first solute is higher in mixture rate than the second solute. For example, the mixture ratio is preferably such that (first solute:second solute)=(4:1).

A solution resulting from the above-described mixture is allowed to adhere to the bearing components as a liquid film (adhesion step). In the description of the present embodiment, the rolling bearing 10 as a whole is immersed in the solution. However, any other technique may be used to allow the liquid film to adhere to the bearing components. The liquid film may be allowed to adhere to the bearing components when the bearing components are separated from one another rather than after the bearing components are assembled together.

Then, the liquid film adhering to the bearing components is hardened. A specific method is to heat the rolling bearing 10 (hold the rolling bearing 10 in a thermostatic tank at 100° C. for 60 minutes) to allow the film (liquid film) to undergo a hardening reaction. Consequently, the solid film 15 is formed on the surface of each of the bearing components (film formation step). A temperature set for hardening of the liquid film may be 50° C. to 150° C. However, the temperature needs to be equal to or lower than tempering temperatures of the bearing components.

The rolling bearing 10 with the solid film 15 formed on each of the bearing components is rotated forward and backward. In other words, the inner ring 11 and the outer ring 12 are rotated forward and backward relative to each other (rotation step). This allows sticking of the rolling bearing 10 via the solid film 15 to be released. Even if protruding portions are present in the solid film 15 formed on a raceway of each of the inner ring 11 and the outer ring 12, the protruding portions can be crushed or removed by the balls 13 to reduce a variation in the thickness of the solid film 15. When the thickness of the solid film 15 on the raceway varies, a problem such as vibration or a variation in torque may occur during rotation of the bearing. In the rotation step, an excessively low rotation speed or an excessively short rotation duration makes an effective reduction in a variation in the thickness of the solid film 15 unlikely to be achieved. An excessively high rotation speed or an excessively long rotation duration of the rolling bearing 10 causes the solid film 15 to be excessively worn off. Thus, preferably, the rotation speed is 1000 to 2000 rpm, and the rotation duration is approximately 3 to 10 seconds.

After being rotated as described above, the rolling bearing 10 is washed in a washer fluid (washing step). The washer fluid used in this step contains the same lubricant (perfluoropolyether: PFPE oil) as that which is used in the adhesion step and which is a fluorine polymer having no functional group; the lubricant has been added to a volatile solvent. The solvent used for the washer fluid is also the same as the solvent that is used in the adhesion step and that is the mixture of ethyl nonafluoroisobutyl ether and ethyl nonafluorobutylether. In other words, the rolling bearing 10 is washed in a washer fluid prepared by diluting perfluoropolyether serving as a solute and having no functional group with the solvent that is mixture of ethyl nonafluoroisobutyl ether and ethyl nonafluorobutyl ether.

The rolling bearing 10 is immersed in the washer fluid as described above and washed using an ultrasonic washing machine. This enables removal of peeled-off films and the like remaining inside the bearing and allows the washer fluid to adhere uniformly and thinly to the surface of the solid film 15 on each of the bearing components as a liquid film. A washing duration is approximately 1 to 3 minutes.

Then, the rolling bearing 10 is taken out of the washer fluid, and the liquid film adhering uniformly and thinly to the solid film 15 is dried (drying step). A specific method is to heat the rolling bearing 10 (hold the rolling bearing 10 in a thermostatic tank at 80° C. for 5 minutes) to dry the film (liquid film). Consequently, the entire surface of the solid film 15 is covered with the lubricant of the fluorine polymer. In other words, the solid film 15 that contains the fluorine polymer dispersively added thereto and the surface of which is covered with the same fluorine polymer is formed. Thus, the rate of a part of the surface of the solid film 15 occupied by the fluorine polymer is higher than the rate of a part of the interior of the solid film 15 occupied by the fluorine polymer.

The lubricant used for the washer fluid is similar in concentration to the lubricant used as the solution in the adhesion step. In other words, the concentration of the lubricant used for the washer fluid is 0.1 wt % to 3 wt %. The concentration of the lubricant used for the washer fluid is preferably equal to or higher than the concentration of the lubricant contained in the solid film 15, and is equal to or higher than 0.1 wt %. When the lubricant used for the washer fluid has only a low concentration, the lubricant of the fluorine polymer dispersively added to the solid film 15 in the film formation step may be discharged from the solid film 15 in the washing step.

Figure 10:
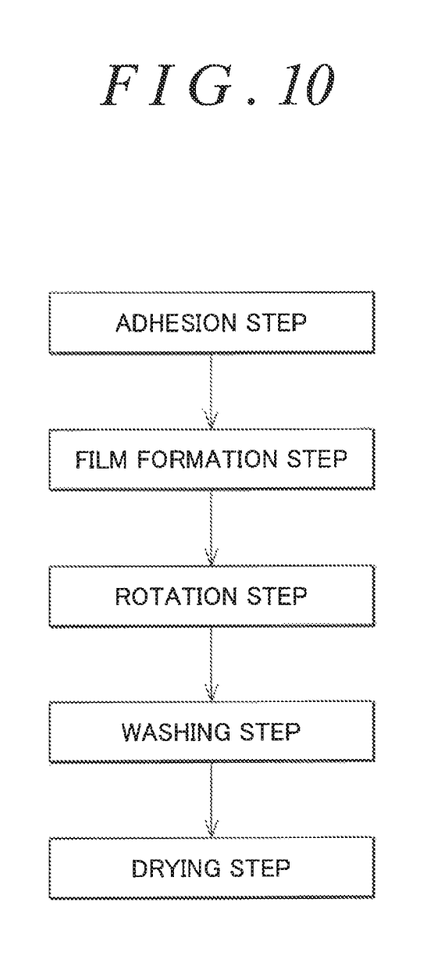
FIG. 10 is a flow diagram illustrating a solid-film formation method.

As described above, the solid-film formation method for forming the solid film 15 on the bearing components of the rolling bearing 10 includes the adhesion step, the film formation step, the rotation step, the washing step, and the drying step, as illustrated in FIG. 10. In the adhesion step, the solution is allowed to adhere to the bearing components as a first liquid film, the solution containing the fluorine compound containing 3-(trimethoxysilyl) propyl methacrylate, hexafluoropropene, and methyl methacrylate as monomer components, and the lubricant (PFPE oil) having no functional group. In the film formation step, the adhering first liquid film is hardened to form the solid film 15 on the bearing components. In the rotation step, the rolling bearing 10 including the bearing components with the solid film 15 formed thereon is rotated. In the washing step, the rolling bearing 10 is washed in the washer fluid containing the same lubricant (PFPE oil) as that used in the adhesion step. The washer fluid (PFPE oil) is allowed to adhere to the bearing components as a second liquid film. In the drying step, the adhering second liquid film is dried. Consequently, the solid film 15 is covered with the lubricant of the fluorine polymer.

The rolling bearing 10 manufactured by this method includes, as the bearing components, the inner ring 11, the outer ring 12, the balls 13 interposed between the inner ring 11 and the outer ring 12, and the cage 14. On the bearing components, the solid film 15 of the fluorine compound is formed that contains 3-(trimethoxysilyl) propyl methacrylate, the hexafluoropropene, and methyl methacrylate as monomer components. The solid film 15 contains the lubricant of the fluorine polymer that is dispersively added to the solid film 15 and that is flowable and has no functional group. The rate of a part of the surface of the solid film 15 occupied by the fluorine polymer is higher than the rate of a part of the film interior (the interior of the solid film 15) occupied by the fluorine polymer.

Figure 5:
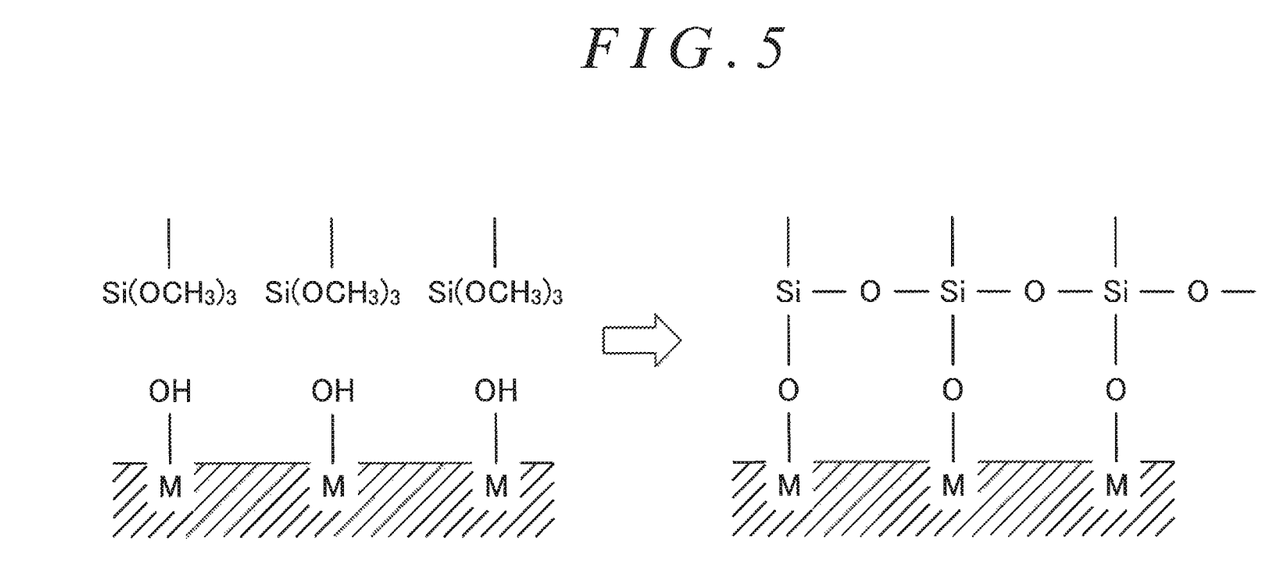
FIG. 5 is a diagram illustrating a solid film.

The resultant solid film 15 has a structure in which molecules are bound together as a result of the hardening reaction. In particular, as depicted in FIG. 5, Si groups in the solid film 15 bind to hydroxyl groups (OH groups) in each bearing component (substrate M) to enhance the adhesion of the solid film 15 to the bearing component. This enables a reduction in the number of dust particles generated from the solid film 15. The bearing component generally has hydroxyl groups (OH groups). The solid film 15 binds firmly to the bearing component due to siloxane bonds and covers the surface of the bearing component. The solid film 15 is thus unlikely to be peeled off and enables a reduction in the number of dust particles generated. The left of FIG. 5 illustrates a state before the hardening reaction, and the right of FIG. 5 illustrates a state after the hardening reaction.

The adhesion step and the film formation step allow formation of the solid film 15 of the fluorine compound in which the lubricant of the fluorine polymer having no functional group is dispersed so as to be flowable. In the washing step and the drying step, the rolling bearing 10 is washed, and the solid film 15 is covered with the lubricant of the fluorine polymer. That is, in the resultant structure, the solid film 15 contains the lubricant of the fluorine polymer dispersively added to the solid film 15 so as to be flowable and having no functional group, and is covered with the lubricant. As described above, the solid film 15 contains the lubricant of the fluorine polymer dispersively added to the solid film 15 so as to be flowable and having no functional group. In other words, the lubricant of the fluorine polymer is flowable due to the lack of functional groups. Consequently, the lubricant oozes through the solid film 15 to contribute to lubrication of the rolling bearing 10, enabling enhancement of lubricity. The rotation step enables a reduction in variation in the thickness of the solid film 15. In this case, even if any fractions of the solid film 15 are peeled off from the solid film 15, the fractions can be removed in the washing step, thus providing a rolling bearing 10 suitable for a clean environment.

In the present embodiment, the lubricant is the fluorine polymer having no functional group, thus enabling the lubrication performance of the rolling bearing 10 to be improved. The fluorine compound (the first solute) has a higher mixture rate than the fluorine polymer (the second solute). This more effectively enhances the adhesion of the solid film 15 to the bearing components. As described above, in the solid film 15 in the present embodiment, the basic resin is a resin containing fluorine (the fluorine compound), to which the fluorine compound having no functional group is added (instead of a conventional solid lubricant).

In the solid-film formation method in the present embodiment, the solution used is prepared by adding the fluorine compound (the first solute) and the lubricant (the second solute, in other words, perfluoropolyether) to the solvent. The solvent is an ether containing at least one of ethyl nonafluoroisobutyl ether and ethyl nonafluorobutylether. This eliminates the need for the use of two types of solvents, that is, the solvent for the fluorine compound (for the first solute) and the solvent for the lubricant (for the second solute, in other words, perfluoropolyether). The washer fluid is prepared by diluting the lubricant (perfluoropolyether) with the solvent (the ether containing at least one of ethyl nonafluoroisobutyl ether and ethyl nonafluorobutylether).

Now, a dust particle life of the resultant solid film 15 will be described. A first example, a first comparative example, and a first conventional example will be described. In the first example, the assembled rolling bearing was degreased and washed, the solution was used to allow the liquid film to adhere to the rolling bearing (adhesion step), the liquid film was hardened (film formation step), the rolling bearing was rotated (rotation step), and the rolling bearing was washed in the washer fluid (washing step) and dried (drying step), as described in the embodiment. The rolling bearing was degreased and washed by using the ultrasonic washing machine to perform washing in hexane for one minute and in acetone for one minute. The liquid film was allowed to adhere by immersing the rolling bearing in the solution for one minute. The liquid film was hardened by being baked at 100° C. for 60 minutes. The rolling bearing was rotated forward and backward such that each of the forward and backward rotations was performed at 1800 rpm for 5 seconds (rotation step). The rolling bearing was washed with the washer fluid for 2 minutes and then dried in the thermostatic tank at 80° C. for 5 minutes. When the rolling bearing was rotated, an axial load that was 5% of a rated load was applied.

In the first example, in the solution, the first solute (the fluorine compound) was 2 wt % in concentration, the second solute (perfluoropolyether having no functional group) was 0.5 wt % in concentration, and the mixture ratio of the first solute to the second solute was 4:1. In the washer fluid, perfluoropolyether having no functional group was 0.5 wt % in concentration. The solvent for each of the solution and the washer fluid was the mixture of ethyl nonafluoroisobutyl ether and ethyl nonafluorobutylether. In the first comparative example, the adhesion step and the film formation step were complete as is the case with the first example, but the rotation step, the washing step, and the drying step were omitted. The first conventional example is a rolling bearing provided with a solid film of fluorine-containing polyurethane polymer compound described in Description of the Related Art (JP H9-137830 A).

Figure 6:
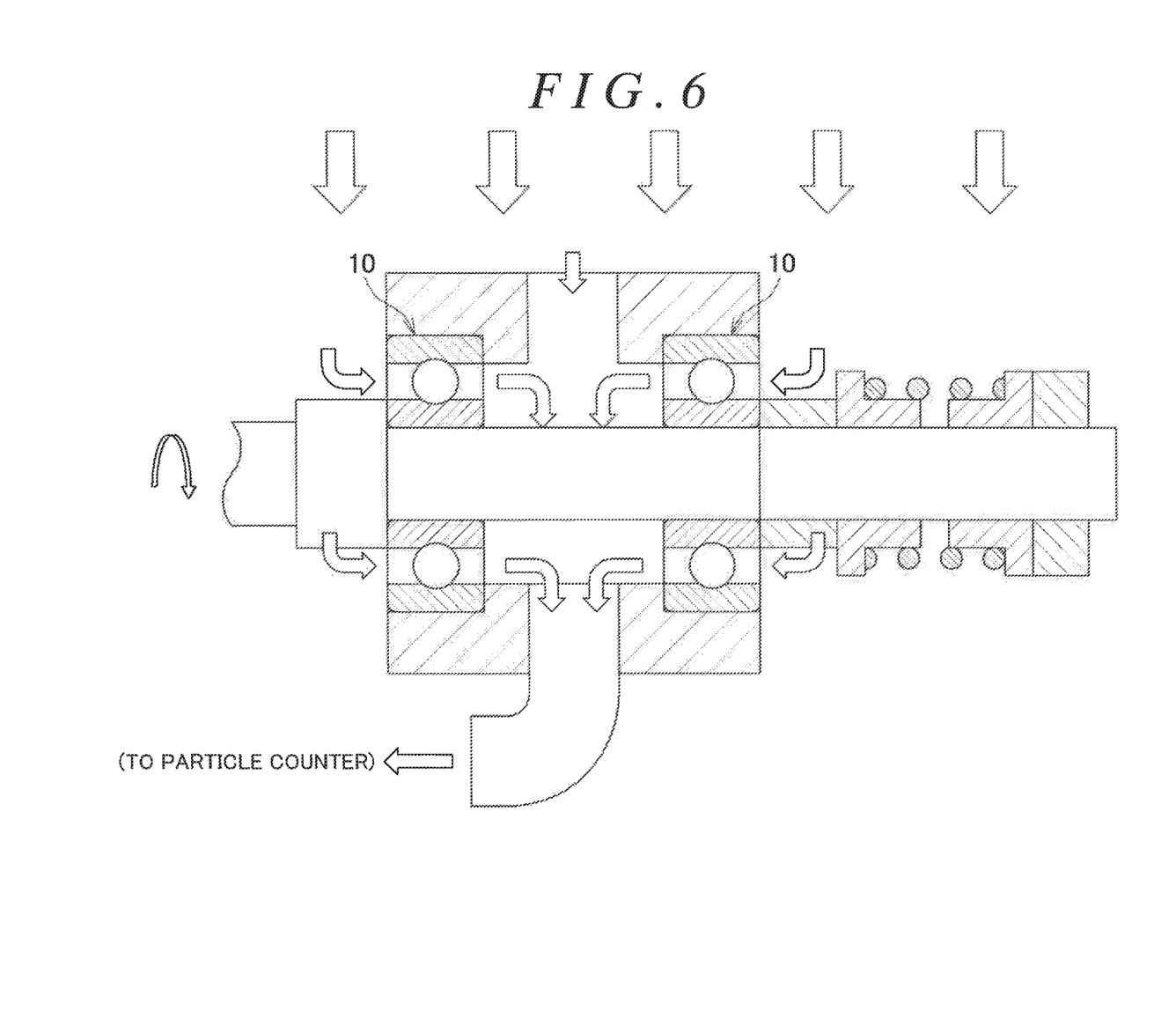
FIG. 6 is a diagram illustrating an apparatus for dust particle tests.
Figure 7:
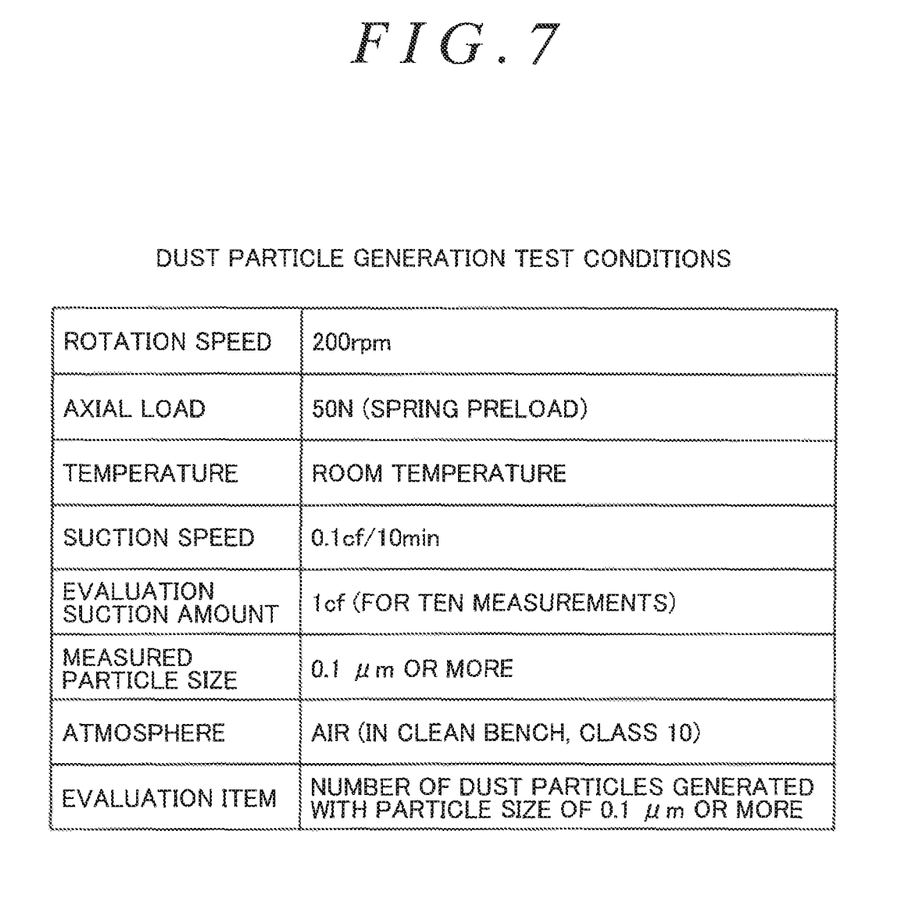
FIG. 7 is a diagram illustrating test conditions.

The rolling bearings in the first example, the first comparative example, and the first conventional example were each attached to an apparatus depicted in FIG. 6, and dust particle generation tests were conducted. Arrows in FIG. 6 indicate flows of air (clean air). The air flows through the bearing to a particle counter. Test conditions are as follows.

Figure 8:
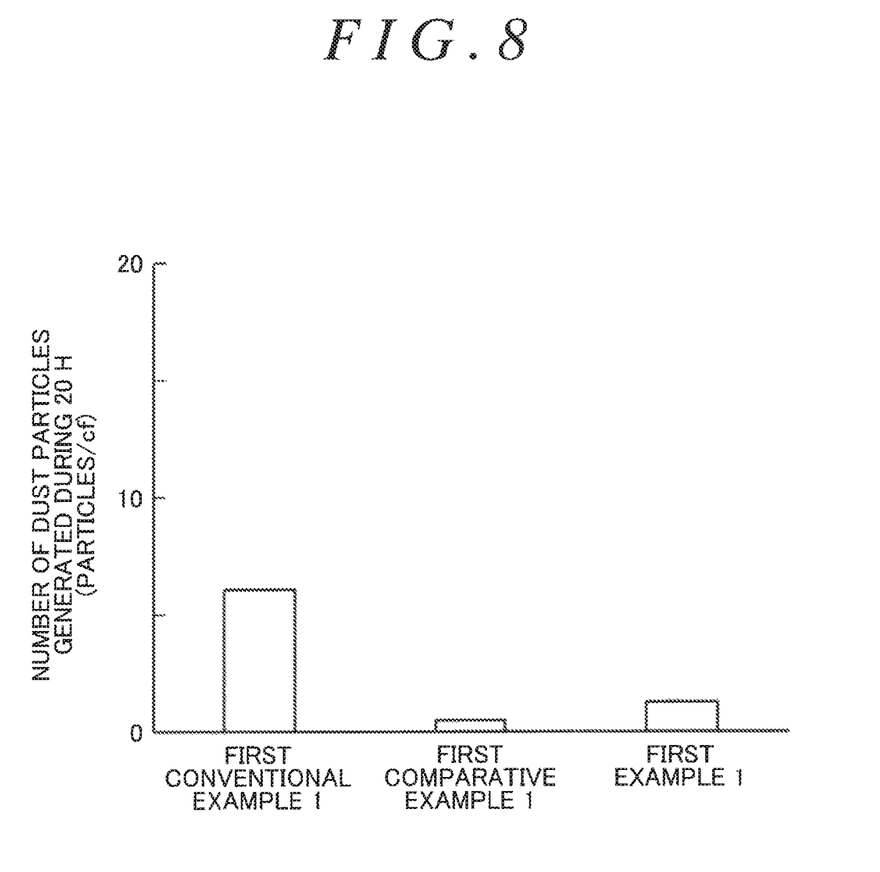
FIG. 8 is a graph illustrating the average number of dust particles (particles/cf) generated during 20 hours.
Figure 9:
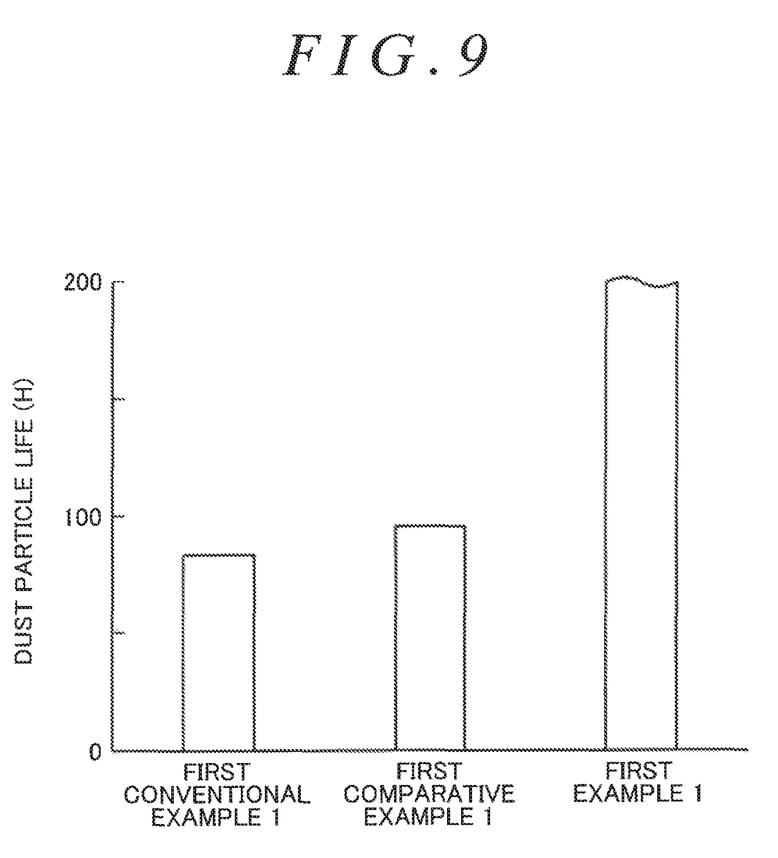
FIG. 9 is a graph illustrating periods until the time when the number of dust particles exceeds a class 10 level (in other words, dust particle life)

FIG. 8 is a graph illustrating the average number of dust particles (particles/cf) generated during 20 hours since the start of the tests. FIG. 9 is a graph illustrating periods until the time when the number of dust particles exceeds a class 10 level (in other words, a dust particle life). As depicted in FIG. 8, the average number of dust particles in the first example is smaller than the average number of dust particles in the first conventional example, and thus, the first example produced a preferable result. As depicted in FIG. 9, the dust particle life in the first example is longer than the dust particle life in the first conventional example, and thus, the first example produced a preferable result.

As described above, in the rolling bearing 10 (first example) in the present embodiment, the solid film 15 adheres more appropriately to the bearing components, thus reducing the number of dust particles generated from the solid film 15. The results of the tests (see FIG. 9) indicate that the solid film 15 in the present embodiment can exhibit high durability. The lubricant oozes through the solid film 15 to contribute to lubrication of the rolling bearing 10, allowing lubricity to be enhanced.

In the above-described embodiment, the inner ring 11, the outer ring 12, the balls 13, and the cage 14 are assembled together, and the assembly is immersed in the solution to form the solid film 15. However, the bearing components in a separated state may be immersed in the solution to form the solid film 15 on each of the bearing components before the bearing components are assembled together. In the description, the solid film 15 is formed on all of the inner ring 11, the outer ring 12, the balls 13, and the cage 14. The solid film 15 may be formed on at least one of the bearing components. In this case, the solution may be allowed to adhere to at least one of the bearing components as the liquid film, and subsequently, the liquid film may be hardened. Furthermore, the bearing components may be washed in the washer fluid and dried. Then, the bearing components may be assembled into the rolling bearing 10, that is, a finished product. Moreover, the rolling bearing 10 depicted in FIG. 1 includes the cage 14. However, the invention may be applied to a rolling bearing from which the cage 14 is omitted.

The solid film 15 need not be formed all over each bearing component but may cover a part of the bearing component. For example, for the inner ring 11 and the outer ring 12, the solid film 15 may be formed on at least a raceway surface contacted by the rolling elements (balls 13). When the cage 14 is in sliding contact with a part of the inner ring 11 or the outer ring 12, the solid film 15 may be formed on that part. Alternatively, the solid film 15 may be formed exclusively on the (entire) surface of each of the rolling elements (balls 13) included in the bearing components.

The solid-film formation method may be intended for rotating machine elements other than such a rolling bearing as depicted in FIG. 1. The solid film may be formed on components of such a rotating machine element. The rotating machine element having the components on which the solid film is formed by the solid-film formation method may be a linear motion element such as a ball screw or a linear guide which includes components arranged in rolling contact with other components.

The embodiment disclosed above is illustrative in every way and is not restrictive. In other words, the rolling bearing in the invention is not limited to the illustrated form but may be in any other form within the scope of the invention.

The rolling bearing (rotating machine element) in the invention enables a reduction in the number of dust particles generated from the solid film and allows the lubricant to ooze through the solid film to contribute to lubrication of the rolling bearing (rotating machine element), enabling lubricity to be enhanced. The solid-film formation method in the invention enables the rolling bearing (rotating machine element) as described above to be manufactured.

What is claimed is:

1. A solid-film formation method for forming a solid film on at least one of bearing components of a rolling bearing including, as the bearing components, an inner ring, an outer ring, and a plurality of rolling elements interposed between the inner ring and the outer ring, the solid-film formation method comprising:

allowing a solution containing a fluorine-containing component and a lubricant having no functional group to adhere to the at least one of the bearing components as a first liquid film;

forming the solid film on the at least one of the bearing components by hardening the adhering first liquid film;

rotating the rolling bearing including the bearing component provided with the solid film;

washing the rolling bearing in a washer fluid containing the same lubricant as the lubricant used in allowing the solution to adhere to the bearing component, and allowing the washer fluid to adhere to the bearing component as a second liquid film; and drying the adhering second liquid film.

2. The solid-film formation method according to claim 1, wherein the fluorine-containing component contains 3-(trimethoxysilyl) propyl methacrylate, hexafluoropropene, and methyl methacrylate as components.

3. The solid-film formation method according to claim 2, wherein the solution is prepared by adding the fluorine-containing component and the lubricant to a solvent, the lubricant is perfluoropolyether, the solvent is an ether containing at least one of ethyl nonafluoroisobutyl ether and ethyl nonafluorobutylether, and the washer fluid is prepared by diluting the lubricant with the solvent.

4. The solid-film formation method according to claim 1, wherein in the solution, the fluorine-containing component has a higher mixture rate than the lubricant.

5. The solid-film formation method according to claim 2, wherein
in the solution, the fluorine-containing component has a higher mixture rate than the lubricant.

6. The solid-film formation method according to claim 3, wherein
in the solution, the fluorine-containing component has a higher mixture rate than the lubricant.

7. A rolling bearing comprising:
an inner ring, an outer ring, and a plurality of rolling elements interposed between the inner ring and the outer ring as bearing components, wherein
at least one of the bearing components is provided with a solid film of a fluorine-containing component containing 3-(trimethoxysilyl) propyl methacrylate, hexafluoropropene, and methyl methacrylate as components,
the solid film contains a lubricant dispersively added to the solid film and having no functional group, and
a rate of a part of a surface of the solid film occupied by the lubricant is higher than a rate of a part of an interior of the solid film occupied by the lubricant.

8. A rotating machine element comprising:
a component member that is rolling contact with another component member, wherein
the component member is provided with a solid film of a fluorine-containing component containing 3-(trimethoxysilyl) propyl methacrylate, hexafluoropropene, and methyl methacrylate as components,
the solid film contains a lubricant dispersively added to the solid film and having no functional group, and
a rate of a part of a surface of the solid film occupied by the lubricant is higher than a rate of a part of an interior of the solid film occupied by the lubricant.

9. A solid-film formation method for forming a solid film on a component member of a rotating machine element that is in rolling contact with another component member, the method comprising:
allowing a solution containing a fluorine-containing component and a lubricant having no functional group to adhere to the component member as a first liquid film;
forming the solid film on the component member by hardening the adhering first liquid film;
allowing the rotating machine element including the component member provided with the solid film to perform a rotating operation;
washing the rotating machine element in a washer fluid containing the same lubricant as that used in allowing the solution to adhere to the component member, and allowing the washer fluid to adhere to the component member as a second liquid film; and
drying the adhering second liquid film.

* * * * *